US00PP14225P29

(12) United States Plant Patent
McCown et al.

(10) Patent No.: US PP14,225 P2
(45) Date of Patent: Oct. 14, 2003

(54) CRANBERRY VARIETY NAMED 'HYRED'

(50) Latin Name: *Vaccinium macrocarpon Ait.*
Varietal Denomination: HyRed

(75) Inventors: Brent H. McCown, Madison, WI (US); Eric L. Zeldin, Madison, WI (US); Peter Normington, Pittsville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 8 days.

(21) Appl. No.: 10/172,533

(22) Filed: Jun. 13, 2002

(51) Int. Cl.[7] ..... A01H 5/00
(52) U.S. Cl. ..... Plt./156
(58) Field of Search ..... Plt./156

(56) References Cited

PUBLICATIONS

Anonymous. 'HyRed Cranberry Released' http://www.hort.wise.edu/news/hyred/HyRed%20Cranberry%20Released.htm 2002.*

Viegas, Jennifer. Discovery News "Super Cranberry in the Works" http://dsc.discovery.com/news/briefs/2001119/cranberry.html Nov. 20, 2001.*

Gallepp, George "Researchers Hope that New Cranberry will Brightern the Future for Wisconsin Growers" in University of Wisconsin–Madison CALS News and Features, posted Nov. 5, 2001 http://www.cals.wise.edu/media/news/11_01/hyred_cranberry.html.*

Anonymous. "Super–Cranberries on the Way" Yahooligans! News Nov. 26, 2001 http://www.yahooligans.com/content/news/top_story/200111261.html.*

Anonymous. New Cranberry has More Red Pigment Wisconsin State—Tuesday, Nov. 6, 2001 Business C10.*

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct variety of cranberry is described. The variety has been named 'HyRed' and is derived from a cross of the 'Stevens' variety and Ben Lear No. 8. The 'HyRed' variety exhibits significantly higher red pigment, short seasonal maturity, excellent vigor, and a yield comparable to other commercial varieties.

3 Drawing Sheets

STATEMENT REGARDING FEDERALLY SPONSORED RESEARCH OR DEVELOPMENT

This invention was made in part with United States Government support awarded by the U.S. Department of Agriculture, Cooperative State Research, Education and Extension Service, under grant number WIS04166.

Latin name of the genus and species of the plant claimed: *Vaccinium macrocarpon* Ait.

Variety denomination: HyRed.

BACKGROUND OF THE INVENTION

The present invention relates to a new and distinctive cranberry clonal variety having significantly higher red pigment, short seasonal maturity, improved vigor and a yield at least comparable to other commercial varieties.

The American cranberry, *Vaccinium macrocarpon* Ait., is a small fruit grown in the temperate regions of the world. The United States is presently the major producer of cranberries, with the combined Wisconsin and Massachusetts harvests accounting for about 80% of the total U.S. annual production.

Although the cranberry is well known for its tart flavor, the principal value component is its red pigment (anthocyanin) content, measured as total anthocyanin (TAcy) in mg per 100 grams fresh fruit. The importance of the pigment content is recognized by most processors as they are known to give a color incentive payment for the delivery of cranberries having a TAcy greater than 30. The incentive payment can be economically important, especially during years of low fruit prices.

Unfortunately, cranberry growers in regions with colder fall weather, such as the north-central portion of the United States, often harvest their cultivars before full fruit color development to avoid freezing injury and icing problems in the low-lying cranberry beds. As a result, regions with a longer growing season, such as Washington and Oregon, produce cranberries with average TAcy levels of 50–60 mg of red pigment/100 gms, whereas cranberries grown in Wisconsin average a TAcy level at 33 mg/100 gms.

Cranberry selections grown today have not yet experienced the extensive breeding as seen in other fruit-bearing species. Many selections were derived directly from native areas or from managed beds of mixed origin. For example, 'Ben Lear' (unpatented) is a cranberry selection taken directly from the wild in Wisconsin in the early 1900s, and is widely grown in short-seasonal areas due to its early fruit development and high color content. The average TAcy content for 'Ben Lear' in Wisconsin is a TAcy of 42.

The U.S. Department of Agriculture undertook, in cooperation with state experimental stations, one generation of breeding in an attempt to improve U.S. cranberry cultivars. The breeding resulted in the introduction of the 'Stevens' (unpatented) variety in the 1950s. The 'Stevens' variety is today the most widely grown cultivar and is characterized by dependably high yields, but only moderate color development, especially in short-seasonal regions such as Wisconsin (Wisconsin average TAcy of 34). Another cultivar released from this program, 'Pilgrim' (unpatented), is less widely grown than 'Stevens' is characterized by relatively large, but more lightly colored fruit than 'Stevens'.

BRIEF SUMMARY OF THE INVENTION

The present invention relates to a new and distinct cranberry variety. The variety is designated 'HyRed' and is derived from a cross of the 'Stevens' variety and a selection designated as 'Ben Lear #8', (unpatented) which was derived from an open-pollinated population of seedlings of 'Ben Lear'. 'HyRed' exhibits significantly higher red pigment (up to 3 fold higher), short seasonal maturity, excellent vigor, and a yield at least comparable to other commercial varieties.

In 1990, a limited breeding program was launched with the goal of developing for Wisconsin and other regions with short growing seasons, cranberry hybrids that produce dependably high yields of early-maturing, high color fruit. It was hoped that such hybrids would dependably capture available color incentives and provide for an early harvest so as to allow an extended harvest season, thus optimizing harvest and handling operations and reducing the risk of unpredictable late-season weather events.

DETAILED BOTANICAL DESCRIPTION

The distinctive characteristics of the new 'HyRed' variety are summarized in table 1 and described in detail below. The color designations made herein are made with reference to The Horticulture Color Chart, R. F. Wilson (1941).

Figure 1:
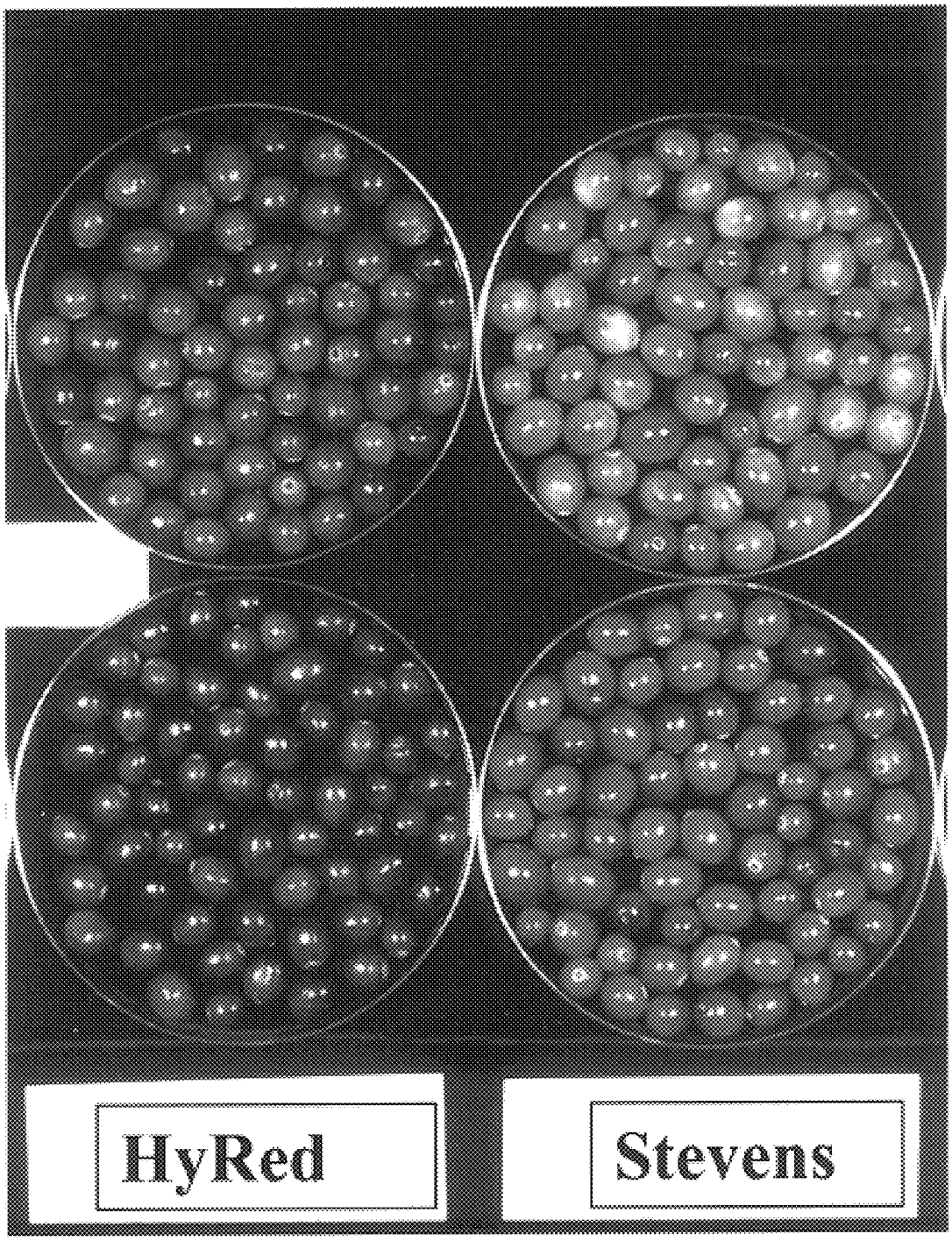
FIG. 1 shows a sample of 'HyRed' fruit as compared to 'Stevens' fruit harvested from the same cranberry bed in Wisconsin: (Top) harvested on Sep. 19, 1996; and (Bottom) harvested on Oct. 3, 1996.
Figure 2:
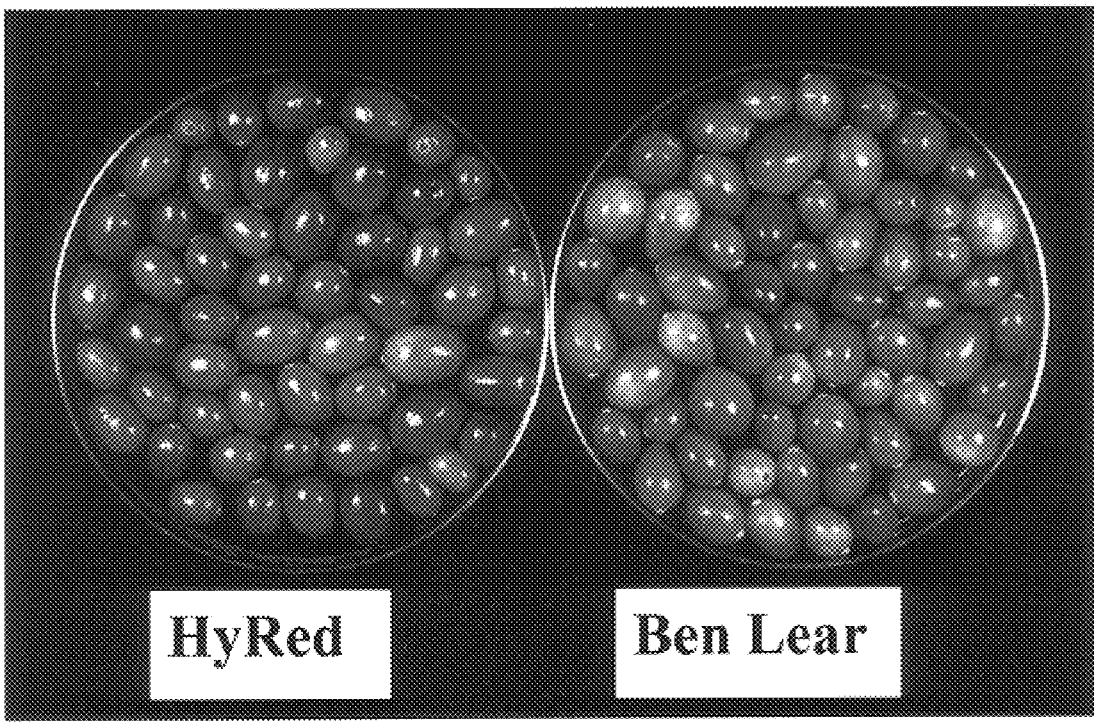
FIG. 2 shows a sample of 'HyRed' fruit as compared to 'Ben Lear' fruit harvested in mid-September from the same cranberry bed in Wisconsin.
Figure 3:
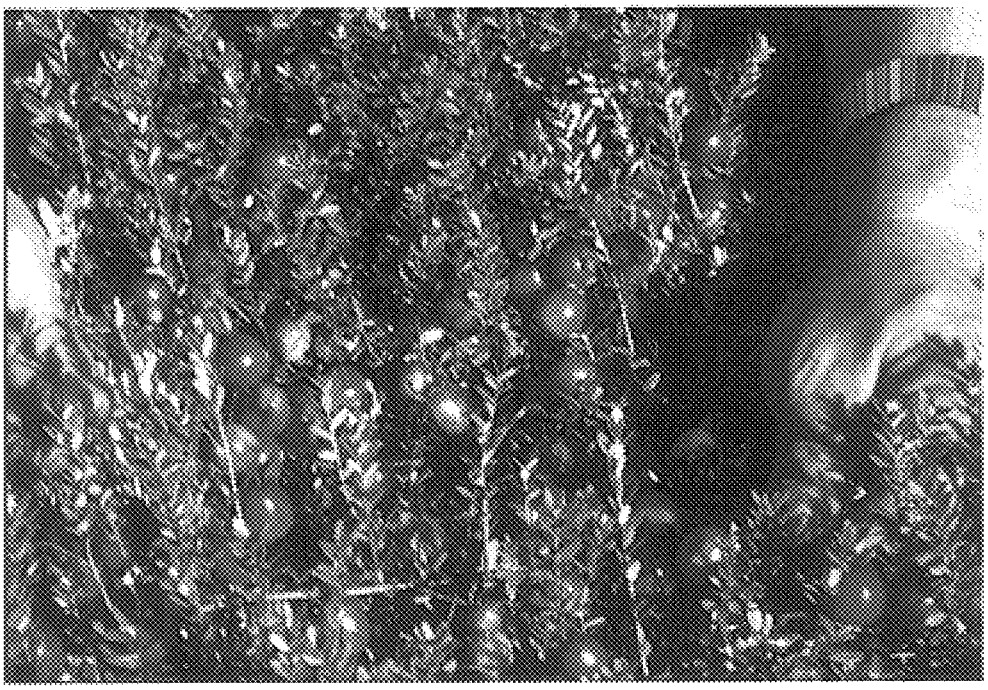
FIG. 3 shows fruiting cranberry vines of 'HyRed' and 'Pilgrim' taken in mid-September from adjacent plots in northern Wisconsin.
Figure 3:
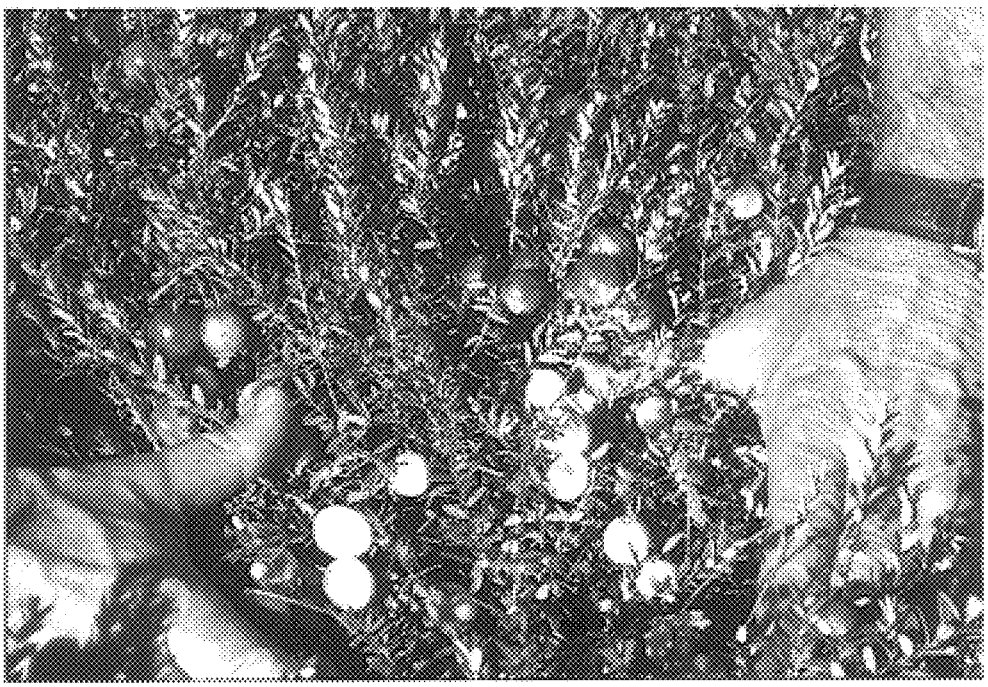

As illustrated in FIGS. 1–3, fruit from the 'HyRed' variety develops excellent coloration even when covered deeply within the vine mat. The 'HyRed' fruit exhibits a color comparable to Carmine No. 21 when fully ripened and has a shape that is somewhat blocky. Although the TAcy content of the 'HyRed' fruit may sometimes reach as high as three times greater than Wisconsin grown 'Stevens' and 'Ben Lear' cultivars, its acidity and sugar content is similar to 'Stevens' and 'Ben Lear'. The 'HyRed' variety flowers, colors, and also ripens earlier than either 'Stevens' or 'Ben Lear', but exhibits a vigor similar to that of the vigorous 'Stevens' selection. 'HyRed' also retains the ease of clonal propagation through cuttings, a common technique for most cranberry selections.

The combination of the above 'HyRed' characteristics easily differentiates 'HyRed', from both its parents, 'Stevens', and the most widely grown cultivar with which it may be confused, 'Ben Lear'. The above characteristics also provide the 'HyRed' variety with benefits not recognized in other commercially grown varieties. For example, the ability of 'HyRed' fruit to develop excellent coloration when covered deeply within the vine mat results in fewer poorly colored berries and provides a more uniform harvest. The early flowering, coloring, and ripening of the 'HyRed' fruit also allows for a harvest earlier than 'Stevens' or 'Ben Lear', if desired, thus optimizing harvest and handling operations and reducing the risk of unpredictable late-season weather events. The similarity of the acidity and sugar content between 'HyRed', 'Stevens' and 'Ben Lear' also allows 'HyRed' to be used in common cranberry products typically dominated by 'Stevens' and 'Ben Lear'.

TABLE 1

Comparison Chart

| Character | HyRed | Stevens | Ben Lear |
|---|---|---|---|
| Typical Fruit Shape | Elliptical blocky with squared shoulders | Elliptical | Elliptical |
| Mid-September TAcy in Wisconsin (mg/100 gms) | >40 | <15 | <20 |
| Mid-September Acidity (Titer) | 2.1–2.6 | 2.2–2.6 | 2.2–2.6 |
| Mid-September Percent Solid (°BRIX) | 7.3–7.7 | 7.3–7.7 | 7.3–7.7 |
| General Vigor | High | High | Medium |
| General Yield | High | High | Medium |
| Flowering Time (compared to Stevens) | 2 weeks earlier | — | 1 week earlier |
| Ripening Period (compared to Stevens) | 2+ weeks earlier | — | 1+ weeks earlier |
| Harvesting Period (compared to Stevens) | 2+ weeks earlier | — | 1+ weeks earlier |
| Cloning by cuttings | Easy | Easy | Easy |

'HyRed' was selected as a single plant from over 700 cloned individual seedlings planted in a test plot in a grower's field in central Wisconsin. The seedlings were derived from a controlled pollination of 'Stevens' and 'Ben Lear #8'. 'Ben Lear #8' is derived from an open-pollinated population of the 'Ben Lear' variety, and originates from a selection by Dr. Don Boone, UW-Madison, from the type collection at DuBay Cranberries, Portage County, Wis. The controlled pollinations were performed in a greenhouse using potted plants, with the resulting seeds germinated in vitro and the resultant plants micropropagated.

'HyRed' was originally selected in 1993 for its early color and high fruit bud set. The selection was then brought back into micropropagation, asexually reproduced, and replanted in test plots of various sizes (20 to 200 $m^2$) from 1994 through 1997. The plantings were done in two distinct growing regions, central Wisconsin and northern Wisconsin. The central Wisconsin region is typified by a 170 day season with nearly 3000 growing degree days (base of 45° F.). The northern region is typified by a 110 day season with 2500 growing degree days. The test plots also included plantings of 'Stevens' or 'Pilgrim' cultivars to serve as standards for comparison. Because of the unique and high cost production techniques required to grow cranberries, areas for test plots were necessarily limited to open space available in commercial beds. Replicated and comparative plots were utilized when feasible.

The 'HyRed' fruit from the 4 to 7 year old plots were sampled periodically, and color analyses performed using procedures based on the method of Fuleki and Francis, "Quantitative methods for anthocyanins: Extraction and determination of total anthocyanin in cranberries", *J. Food Sci.,* 33:72–77 (1968). The samples were taken primarily in mid-September, usually about 2 weeks before the beginning of the commercial harvest. In every year, 'HyRed' presented TAcy readings at least twice that of comparable plots of 'Stevens' (Table 2). 'HyRed' also exhibited prominent early coloration, even in late August, and a greater rate of increase in pigment content than 'Stevens' through the September ripening period (Table 3).

TABLE 2

Comparison between fruit color of 'Stevens' and 'HyRed'

| | TAcy Content Harvest Year1997 | TAcy Content Harvest Year 2000 | |
|---|---|---|---|
| Cultivar | Central Wisconsin | Central Wisconsin | Northern Wisconsin |
| Stevens | 22.2 | 17.1 | 24.6 |
| HyRed | 58.1 | 51.2 | 53.0 |

TABLE 3

Fruit color development of 'Stevens' and 'HyRed' over the 1997 growing season

| | TAcy Content | | | | | |
|---|---|---|---|---|---|---|
| Cultivar | 28-Aug | 3-Sep | 10-Sep | 17-Sep | 24-Sep | 1-Oct |
| Stevens | 5.8 | 9.2 | 12.2 | 22.2 | 31.3 | 44.1 |
| HyRed | 27.4 | 34.2 | 39.3 | 58.1 | 86.3 | 115.2 |

Anthocyanins of cranberry are generally located almost entirely in the epidermal layers of the fruit. One factor which is believed to contribute to high extractable fruit color in cranberry is small fruit size, due in part to the influence of surface area to weight ratio on the total pigment content for each fruit. A negative correlation between yield and some of the flavonoid compounds, including anthocyanins, has also been suggested. However, differences in fruit size and yield between 'HyRed' and other cultivars have been minor when compared to the differences in extractable color. For example, as shown in Table 4, early harvests of fruit from 'HyRed' and the commercial cultivar 'Pilgrim' which is known for its large fruit, in adjacent plots in northern Wisconsin have shown a markedly greater pigment content in 'HyRed', fruit for both years. Differences in fruit yield and fruit size were negligible or much less pronounced. In all plantings, the fruit size of 'HyRed' has averaged above 1.5 g, which is similar to the average fruit size of 'Ben Lear' and 'Stevens' grown in comparable locations in Wisconsin (data not shown). Thus, 'HyRed' appears to be able to develop high levels of extractable pigmentation simultaneously with good fruit size and yield.

TABLE 4

Pigment content, fruit size and total fruit yield comparison

| | Harvest Year 2000 | | | Harvest Year 2001 | | |
|---|---|---|---|---|---|---|
| Cultivar | TAcy Content | Average Individual Berry Weight | Average Total Sample Berry Weight | TAcy Content | Average Individual Berry Weight | Average Total Sample Berry Weight |
| Pilgrim | 17.0 | 1.09 g | 62.8 g | 13.7 | 1.64 g | 60.9 g |
| HyRed | 53.0 | 1.77 g | 61.8 g | 39.4 | 1.60 g | 54.6 g |

In 2000, analyses of two additional fruit quality traits, titratable acidity and percent total soluble solids (° BRIX), was conducted at Ocean Spray Cranberries, Inc. using standard procedures adapted from Ballington et al., "Fruit quality characterization of 11 Vaccinium species," *J. Amer. Soc. Hort. Sci.,* 109:684–689 (1984). Fruit was harvested durinig late September 2000 from adjacent plots at two production locations Wisconsin. Three pooled samples were taken from harvests in randomly tossed rings within the plot at each location. ANOVA indicated no significant differences for a fruit trait (P=0/05) between selections at a location. As illustrated in Tables 5 and 6, 'HyRed' fruit did not show any significant differences in these traits when compared to either the standard 'Stevens' cultivar or 'Pilgrim' cultivar grown in the same location.

TABLE 5

Titratable acidity and percent total soluble solids comparison, Mid-September harvest samples, central Wisconsin.

| Cultivar | Titratable acidity (meq/g dry wt) | °BRIX |
|---|---|---|
| Stevens | 2.40 | 8.64 |
| HyRed | 2.40 | 8.47 |

TABLE 6

Titratable acidity and percent total soluble solids comparison, Mid-September harvest samples, northern Wisconsin.

| Cultivar | Titratable acidity (meq/g dry wt) | °BRIX |
|---|---|---|
| Pilgrim | 2.46 | 7.54 |
| HyRed | 2.41 | 7.94 |

We claim:

1. The new and distinct variety of cranberry plant herein described and illustrated, and identified by the characteristics enumerated above.

* * * * *

(A)

(B)